(12) United States Patent
Göbel

(10) Patent No.: US 11,690,947 B2
(45) Date of Patent: Jul. 4, 2023

(54) DEVICE AND METHOD FOR THE LAVAGE-TYPE INTRODUCTION OF A FECAL TRANSPLANT OR OF A THERAPEUTICALLY EFFECTIVE SUBSTANCE INTO THE COLON OF A PATIENT

(71) Applicant: Advanced Medical Balloons GmbH, Waghäusel (DE)

(72) Inventor: Fred Göbel, Speyer (DE)

(73) Assignee: Advanced Medical Balloons GmbH

( * ) Notice: Subject to any disclaimer, the term of this patent is extended or adjusted under 35 U.S.C. 154(b) by 1125 days.

(21) Appl. No.: 16/180,185

(22) Filed: Nov. 5, 2018

(65) Prior Publication Data

US 2019/0192836 A1 Jun. 27, 2019

Related U.S. Application Data

(63) Continuation-in-part of application No. PCT/IB2017/001458, filed on Nov. 27, 2017.

(30) Foreign Application Priority Data

Nov. 25, 2016 (DE) .................. 10 2016 014 053.4
Nov. 4, 2017 (DE) .................. 10 2017 010 234.1

(51) Int. Cl.
*A61M 1/00* (2006.01)
*A61M 3/02* (2006.01)
(Continued)

(52) U.S. Cl.
CPC ........... *A61M 1/77* (2021.05); *A61B 10/0038* (2013.01); *A61F 5/442* (2013.01); *A61M 3/0212* (2014.02);
(Continued)

(58) Field of Classification Search
CPC ....... A61B 10/0038; A61B 1/31; A61F 5/442; A61M 3/0295; A61M 31/00; A61M 3/022;
(Continued)

(56) References Cited

U.S. PATENT DOCUMENTS

2011/0160657 A1* 6/2011 Gobel ................ A61F 5/445
604/328

FOREIGN PATENT DOCUMENTS

DE 338976 7/1921
DE 102008055674 12/2009
(Continued)

*Primary Examiner* — Theodore J Stigell
*Assistant Examiner* — Rachel T. Smith
(74) *Attorney, Agent, or Firm* — Pandiscio & Pandiscio

(57) ABSTRACT

A device and a method for a lavage-type introduction of a stool transplant or of another, local or topically effective substance through the anus into the colon of a patient, wherein the substance to be introduced is flushed also into the upper parts of the colon of the patient in a torrent-like manner through correspondingly large-lumen catheters; said device comprises an ano-rectal placed head part remaining inside the patient from the beginning until the end of the application and a system of exchangeable bags, which are connectable to the head part, whereby two different types of bags can be applied, one of which is designed for the cleaning lavage, while the another is designed for the introduction of a substance or a transplant.

15 Claims, 3 Drawing Sheets

(51) Int. Cl.
  *A61F 5/442* (2006.01)
  *A61B 10/00* (2006.01)
  *A61M 31/00* (2006.01)
  *A61F 5/445* (2006.01)
  *A61B 1/31* (2006.01)

(52) U.S. Cl.
  CPC ........ *A61M 3/0229* (2013.01); *A61M 3/0245* (2013.01); *A61M 3/0283* (2013.01); *A61M 3/0295* (2013.01); *A61M 31/00* (2013.01); *A61B 1/31* (2013.01); *A61F 2005/4455* (2013.01); *A61M 3/022* (2014.02); *A61M 3/0208* (2014.02); *A61M 2202/068* (2013.01); *A61M 2205/04* (2013.01); *A61M 2210/1064* (2013.01)

(58) Field of Classification Search
  CPC .............. A61M 2202/068; A61M 3/02; A61M 3/0229; A61M 3/0241; A61M 2210/1064; A61M 2210/106; A61M 2210/1067
  See application file for complete search history.

(56) References Cited

FOREIGN PATENT DOCUMENTS

| | | |
|---|---|---|
| DE | 102012003034 | 8/2012 |
| EP | 0254410 | 1/1988 |
| EP | 1784140 | 2/2012 |
| WO | WO 2009/144028 | 12/2009 |
| WO | WO 2013/026564 | 2/2013 |

\* cited by examiner

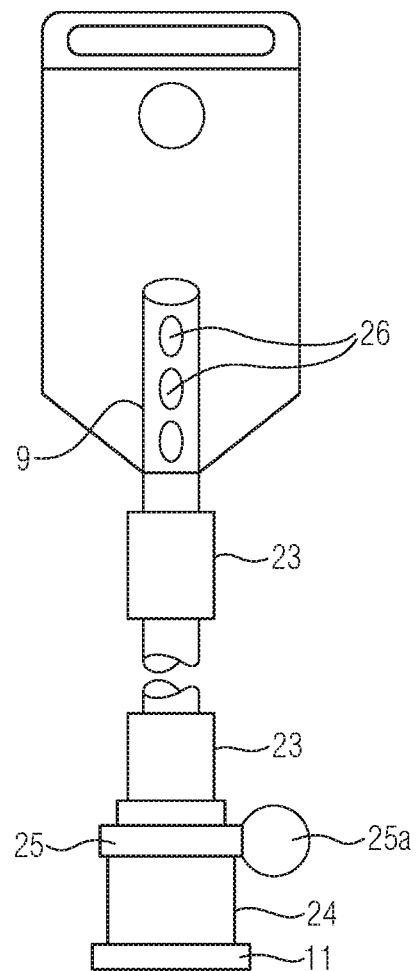

DEVICE AND METHOD FOR THE LAVAGE-TYPE INTRODUCTION OF A FECAL TRANSPLANT OR OF A THERAPEUTICALLY EFFECTIVE SUBSTANCE INTO THE COLON OF A PATIENT

REFERENCE TO PENDING PRIOR PATENT APPLICATIONS

This patent application:

(i) is a continuation-in-part of International (PCT) Patent Application No. PCT/162017/001458, filed 27 Nov. 2017 by Advanced Medical Balloons GmbH for DEVICE FOR THE REPETITIVE SUPPLY AND DRAINING OF SUBSTANCES FOR MEDICAL THERAPY, AND SYSTEM AND METHOD FOR PRODUCING FAECAL CONTINENCE BY INTERMITTENT COLON LAVAGE BY MEANS OF A PERMANENTLY PLACED TRANS-ANAL OCCLUDING OR ACCESS CATHETER, which claims benefit of German Patent Application No. DE 10 2016 014 053.4, filed 25 Nov. 2016; and (ii) claims benefit of German Patent Application No. DE 10 2017 010 234.1, filed 4 Nov. 2017.

The three (3) above-identified patent applications are hereby incorporated herein by reference.

FIELD OF THE INVENTION

Medically indicated transfers of stool from a donor to a receiving patient are performed with increasing frequency. Especially in the treatment of chronic inflammatory diseases of the colon, good therapeutic results are achieved with so-called stool transplantations.

BACKGROUND OF THE INVENTION

In order to render the transfer of stool from a donor to a receiving patient as efficient as possible, customarily the colon of the receiving patient is, prior to the transplant procedure, initially normally defecated, and subsequently, the colon is purged of the remaining residues of stool. Subsequently, the stool to be transplanted is introduced either anterograde, from the oral side, endoscopically into the upper part of the small intestine, or retrograde, from the anus, via an ano-rectal enema into the colon of the patient. In both cases, the stool transplant is in a suspended state, normally in a highly fluid state.

Besides the efficiency of the preparative removal of the patient's microbiome, the success of the transfer depends particularly on the size of the achieved contact surface between the introduced stool and the receiving colon, as well as on the duration of the exposure with the stool transplant.

Nowadays, conventional enema systems generally used for the retrograde, ano-rectal transfer of stool comprise a shaft, which is to be introduced into the anus and which is provided with a retention balloon positioned in the rectal ampulla. The stream efficient diameter of such systems is small and does not allow either an efficient rinsing (lavage) of the colon, or an efficient large-area wetting of the colon surface with the stool suspension. The shaft bodies of conventional enema systems are normally made of relatively rigid materials, which do not exclude an accidental perforation of the colon wall by the shaft. For this reason, the recommended trans-anal utilisation period of a conventional enema system is limited to a few minutes. Principally, the application generally requires a continuous control by the applicant. Furthermore, commercially available enema systems are incapable of sealing against intestinal contents trickling or leaking out of the anus during the procedure. Certainly, by a contraction of the sphincter, the patient can transiently suppress the running out of intestinal contents, but after a few minutes of contraction the sphincter muscle gets tired and the intestinal contents or the rinsing solution leak out passing around the catheter shaft. Many patients usually perceive the firmly widened elastic retention balloon in the rectum as a foreign object. Some patients respond to the stimulus, which is initiated by the firm retention balloon in the rectum, with a reflective contraction of the rectum and with an opening of the anus.

SUMMARY OF THE INVENTION

The present invention overcomes these disadvantages by optimizing of the sealing performance in the anus, by minimizing the irritations typically resulting from a foreign body, by facilitating the entry of the substances to be instilled in the colon into the upper portions of the colon, by rendering the contact time between the substances deposited in the colon and the intestinal surface extendable to an arbitrarily long period of time, as well as by allowing the entry of thick, viscous transplants or substances into the colon. Together with the described device, the receiving or treated patient may, in case of need, change from the lying position into a sitting position or even a standing position, without any anal leakage.

A further, decisive advantage of the invention is the option according to the present invention of a preceding, cleaning lavation and preparation of the colon, which is subsequently followed by the instillation of the transplant or of the respective agent. Thereby, the patient-sided portion of the device, especially the trans-anally placed head unit, may remain in the rectum, while the vessel, which is terminally connected to the patient-sided catheter, can be exchanged through a respective connecting function, depending on the phase of the procedure, that is either lavage or instillation.

The device described in the following and the method enabled by the device, for a combined flushing-type cleaning lavage and a flushing-type therapeutical instillation especially facilitates repeated cycles of inflow into the colon and outflow from the colon, whereby in the inflow phase, the bag with the applied medium (rinsing solution for cleaning, stool transplant, pharmacological agent) is raised above the patient, and in the outflow phase, the bag is lowered below the level of the patient, so in summary a so-called "pivoting" enema is executed.

In the case of the initial pivoting lavage with a cleaning liquid, the cycle of raising and lowering is repeated until the intestinal contents drained from the colon are free from shaped residues of the stool. If required, the bag which is used for the lavage, can be exchanged several times and filled with fresh cleaning liquid. The lavage bag, which was used for cleaning the colon, may subsequently be rotated by 180° and be fixed upside down at the lower bed frame, now having a collecting function and receiving, during an arbitrary period of time, the outgoing stool mobilized by the lavage, without contamination of the patient and the surroundings.

During the subsequent introducing of the transplant or of the active agent, the passing into the colon and out of the colon proceeds in a similar way through the repetitive "pivoting". The transplant or the active agent is inserted into an instillation bag similar to the lavage bag, and said bag is then connected the patient-sided portion of the device, which remains in the rectum of the patient during the whole procedure. Through the multiple cycles of flushing-type washing of a large volume of liquid into the colon and outflow of the bag's content from the colon, it is ensured that the mucous membrane of the upper portions of the colon, especially of the transverse colon and of the rightside ascending colon, too, is reached or wetted by the transplant or by the agent.

Due to the particular trans-anal sealing mechanics of the device, which follows the anal sphincter muscle dynamically, the patient can retain the transplant or the substance inside the colon arbitrarily long and in almost every body position, with relaxed sphincter muscle, without the risk of a leakage of the intestinal contents out of the anus. Thus, for the respective application, an optimum exposure time of the medium instilled in the colon can be achieved.

After the end of the phase of the "pivoting" instillation, the respective bag may again be turned upside down and placed below the patient. Thereby, it is given a draining and collecting function, whereby the rest of the implant or of the agent contained in the colon can drain during an arbitrary period of time into the bag. During this phase, the patient may again adopt a comfortably relaxing posture.

With the device described in the context of the invention, also locally or topically active substances may be introduced into the large intestine, especially into its upper portions close to the small intestine. Such an option is of particular importance in the case of chronically inflammatory processes in the area of the junction between ileum and cecum. The introduced topically active substances may, for example, be of antibiotic nature or of non-antibiotic, anti-inflammatory nature, too.

The operating principle of the device is substantially based on a particularly flow-efficient large-lumen in- and outflow of the medium. The inflow and outflow volume stream to and from the patient is adjusted in such a way that, during a return-flow enema with "pivoting" of the bag, a volume of 1000 mL is introduced in less than 30 seconds, preferably in less than 15 seconds, and, preferably, may also be drained in the same amount of time. At such flow values, the substance which is to be introduced for the lavage or for the instillation, is washed as a flush into the colon. Furthermore, the device comprises a throttling function which limits the inflow. In case of an overlarge volume flow to the patient, irritating right up to painful sensations of the colon are possible.

In the context of the invention, for achieving a lavage-type introduction of a cleaning or an instilling liquid, volumes from 1000 to 2000 mL, preferably from 1200 to 1500 mL, are used and are filled into the respective vessels or bags in such an amount.

The inner diameters of all segments of the device are designed in such a way that the flow volumes as described above can be achieved. They are measured from 12 to 22 mm, preferably from 15 to 20 mm.

BRIEF DESCRIPTION OF THE DRAWINGS

The structural and functional features of the device according to the invention are depicted in the following figures.

FIG. 6 shows a further vessel implemented as a bag, which is optimized for the large-volume lavage-type instillation of a therapeutical substance into the patient's colon.

DETAILED DESCRIPTION OF THE PREFERRED EMBODIMENTS

Figure 1:
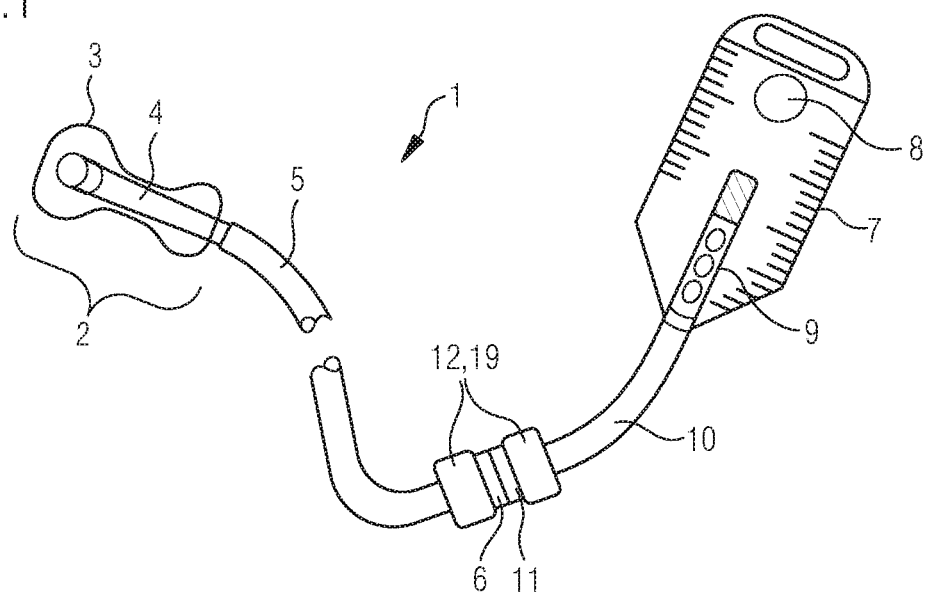
FIG. 1 shows a device for the lavage-type repetitive pivoting introduction of a cleaning liquid into the colon, said device comprising the patient's sided portion as well as the bag's sided portion, in a schematic overview.

FIG. 1 shows a device according to the invention, for the lavage-type "washing in" of a substance into the colon of a patient. Said device comprises an anorectal placed head portion 2 remaining in the patient's anus over the whole duration of the procedure. Said head portion 2 comprises a dumbbell-shaped or a mushroom-shaped balloon element 3, which combines the functions of a rectal retension and a trans-anal sealing and is mounted on a shaft element 4. Said shaft element 4 becomes elastically radially deformed or folded when a force is applied on the wall of the shaft, and when the force in the anal channel is decreasing, spontaneously said shaft element 4 straightens up elastically. Upon an axial deflexion of the shaft's tube, said shaft element transforms from its trans-anal rest position into a single or multiple axial buckling, whereby any likelihood of potential perforations of the colon wall due to a shifting of the head portion of the drainage device into the upper intestines is almost excluded. Said shaft element 4 can optionally have a corrugated, wavy profile. In such a case, by use of elastic materials (for example, polyurethane), good self-erecting properties can be achieved even at relatively small wall thicknesses of the shaft element. Furthermore, after overcoming of a special initial force for the transition of the shaft into the folded or compressed state, the radial folding and the axial compression of the shaft wall can proceed with a lower necessary force in the course of the further deformation of the shaft profile. Thereby, the radial and axial deformation is relieved in comparison to the initial deformation.

A tube part 5 adjoins to the shaft tube proximally, which transitions at the free end into a catheter-sided connector element 6. The connector enables a reversibly detachable connection to a preferably bag-shaped vessel 7, which can be filled through a closable opening 8. The vessel 7 comprises a tube element 10, which changes over into a connector element 11, which is compatible with the connector 6. In the transition area to the tube 10, the vessel 7 integrates a flow restricting function 9, which either presets the outflow from the vessel fixedly through the number and size of openings, or is variably adjustable. Additionally to a bag-sided integrated throttling or closing element, a separately implemented, simple, clamp-type or slidable closing element 12 can be inserted into the tube element optionally, preferably close to the connector.

Figure 2:
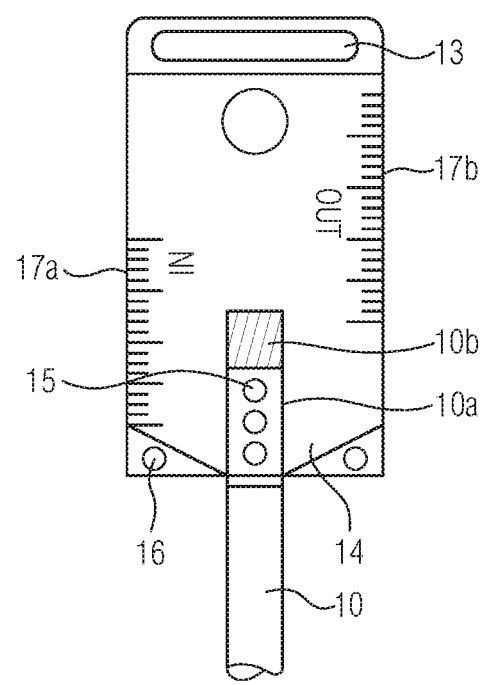
FIG. 2 shows an embodiment of a combined lavage and collection bag for an optional lavage-type cleaning of the colon preceding the instillation of the substance.

FIG. 2 shows a vessel 7 according to the invention, which is implemented as a foil bag and primarily performs the function of a lavage-type cleaning colon rinsing, which precedes the "washing in" of the substance to be instilled in the application procedure. The bag comprises a handle 13 at the upper end. Preferably, the bag comprises only a single chamber, in which, during the pivoting procedure, the fresh flushing medium mixes with the content drained from the colon. The chamber is filled through an opening 8 at the upper end of the bag and is closed in a leakproof manner. At the bottom, the bag comprises an outlet portion 14, where a tube connector 10a is welded. Outwardly, the combined inlet and outlet tube 10 adjoins to said tube connector. Inwardly, said tube connector lines up with a thin-walled tube portion 10b, which has a valve-like function within the bag. The portion of said tube connector 10a, which protrudes inside the bag, is perforated. On the one hand, this special type of construction of said tube connector allows to separate formed stool, which is already in the bag, and to feed back only fluid content of the bag to the patient for the further irrigation. On the other hand, the volume stream can be throttled or restricted through the perforations 15 of said tube connector in a fixed, that means not adjustable manner. The tube 10 outgoing from said tube connector should have a length from approx. 1.0 to 1.7 m, preferably from 1.3 to 1.5 m.

By means of the handle 13, the bag can be pivoted comfortably during the cleaning procedure. After the completion of the raising and lowering cycles, the bag is turned upside down and fastened at a level below the patient in a thenceforth collecting function. On its bottom edge, the bag comprises respective openings 16 for an upside down hanging position. Furthermore, it comprises a scale 17a for the detection of the inlet volume used for the cleaning (in-scale) and an out-scale 17b for the detection of the volume entirely received from the colon of the patient. Therefore, a balance can be made for the cleaning procedure, and the rest volume remaining inside the colon can be determined.

Figure 3:
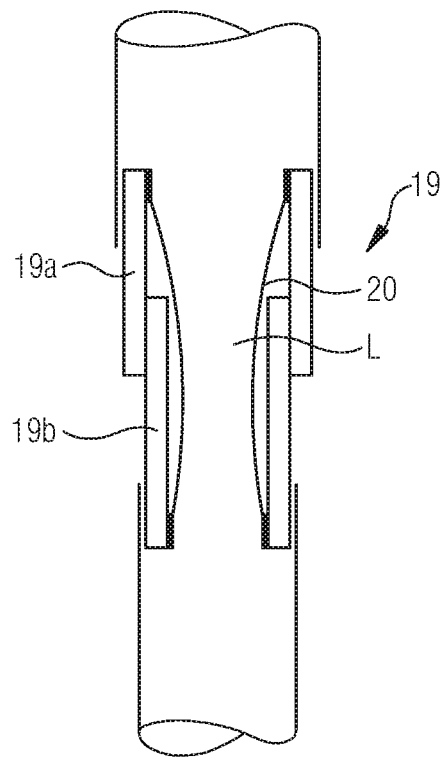
FIG. 3 depicts a special flow limiting or throttling function inside of the in- and outflow tube system, on the basis of the torsion of a tube.

FIG. 3 shows a possible embodiment of the functional element 19, which combines the throttling, that means flow restricting function and the closing function. The mechanism comprises two sleeves 19a and 19b arranged coaxially to each other, which can rotate against each other around their common axis or which can be twistable relative to each other to a certain angle value, whereby a foil tube element 20 is arranged inside the sleeves 19a, 19b preferably coaxially to the common axis of the both sleeves 19a, 19b in such a way that one of its ends is connected to the inner wall of one sleeve part 19a and the other of the both ends is connected to the inner wall of the other sleeve part 19b, which is positioned in an axial alignment. If the sleeves 19a, 19b are twisted relatively to each other around their common axis, for example for an amount from 90° to 270°, or even beyond that, said tube element 20 gradually transitions from its axial aligned, open lumen rest position into a twisted position with closed lumen, whereby the free lumen L of the tube increasingly narrows with increased rotation and finally closes completely. The functional element 19 can be integrated both in the catheter-sided tube segment of the device and also in the bag-sided tube segment, whereby it is preferably arranged as close as possible to the connector.

Figure 3A:
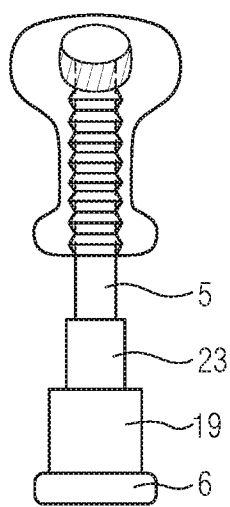
FIG. 3a depicts a preferred arrangement of the throttling function at the proximal end of the patient's sided catheter unit.

As an example, FIG. 3a shows the positioning of the flow controlling functional element 19 in the terminal connector 6 at the tube 5 of the head unit 2. Here, the element 19 serves for sealing the tube during the phase of exchanging the bags, so that the fluid remaining in the intestinals can be kept safe inside the colon, and a leakage through the temporarily opened connector into the surroundings can be avoided. A transparent sleeve element 23 can adjoin immediately distally to the throttle, that means towards the patient, which renders the in- and outflowing fluid or, respectively, its particular quality and the actual volume flow visible. Optionally, a sleeve element or both sleeve elements 19a, 19b can be made out of transparent material.

Figure 4:
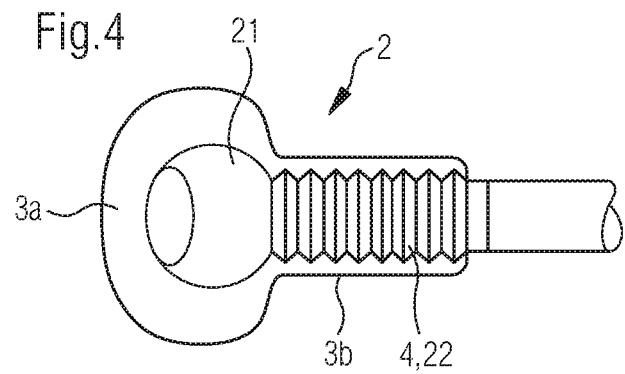
FIG. 4 shows a preferred embodiment of a head unit with a shortened balloon body, remaining inside the patient during the procedure.

FIG. 4 shows an exemplary head unit 2 in detail, whereby it comprises a balloon component 3, which is not dumbbell-shaped, but in a shortened form mushroom-shaped. The proximal portion 3b of the balloon body extends through the anal channel, the distal portion 3a is placed inside the rectum. The trans-anal portion 3b can optionally terminate in line with the outer opening of the anus, the anal ring, or may also extend beyond the plane of the anus as a connector. As a less preferred embodiment, lengths of the portion 3b can be chosen, which would only reach into the anal channel, but do not extend up to its outer opening. The shaft element 4 comprises an olive-shaped or a ring-type extension 21, which facilitates the insertion into the anus. Preferably, the shaft element is made of polyurethane and comprises within its area supporting the balloon a wavy profile 22 aiding the elastic self-erection of the shaft.

Figure 5:
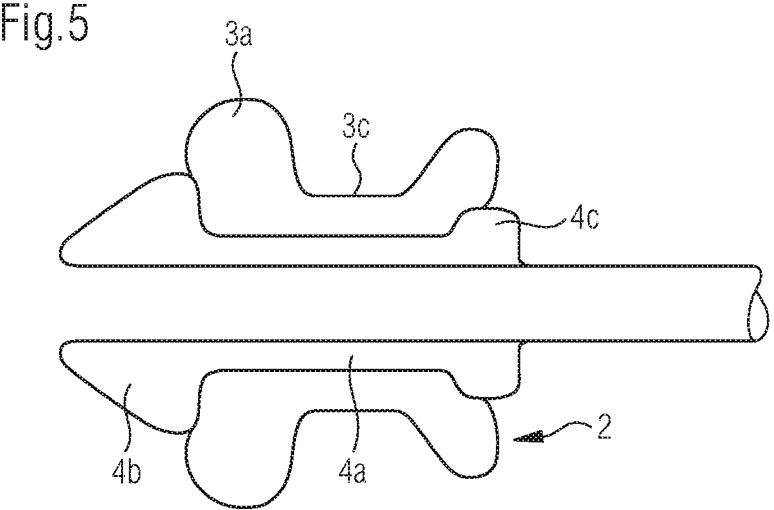
FIG. 5 shows a head unit with a mushroom-shaped distal insertion element.

FIG. 5 shows a further embodiment of the head unit 2, whereby the shaft element comprises a shaft portion 4a supporting the balloon body 3, and a special mushroom-shaped, conical/tapered tip portion 4b. Contrary to the aforementioned embodiments like e.g. in FIG. 4, the balloon body is shortened in its distal intra-rectal portion 3a, but all together yet of a dumbbell shape. Its middle portion 3c is tapered and provides, upon a respective positioning of the balloon tapering, a dynamically adaptive, trans-anally effective seal performance adjusting to the respective rectal pressure, as described in context with the invention. 20a The whole shaft body, that is the tip portion 4b, the proximally adjoining shaft portion 4a as well as a pre-anal adjoining portion 4c, can be cast or injection molded from a soft, foam-like or jelly-like material.

The implementations depicted in FIGS. 4 and 5 of the balloon body comprising an intra-rectal balloon segment with a large diameter and a trans-anal segment extending through the anus or even only into the anus, enable a special sealing dynamics, whereby the respective rectal effecting force is absorbed by the segment 3a, and provides a continuous sealing in the anal channel in the segment 3b in a temporarily synchronous and corresponding manner. All segments of the balloon body are preformed during their manufacturing to their entire working dimensions or alternatively even beyond, that is residually dimensioned. Preferably, the fully shaped balloon is in situ filled incompletely, that is slackly, so the perception of the device as a foreign body is largely avoided. In its slackly filled shape, the balloon adapts in an optimum manner to the respective ana-rectal anatomy an to the respective prevailing rectal force.

FIG. 6 shows a bag-type vessel, which is optimized for the lavage-type washing in or instillation of a substance into the colon of a patient. A sleeve-like handpiece 24 designed for gripping with a hand adjoins to the connector 11, wherein a clamping-type or tongs-like closing element 25 is embedded, which in case of single-handed operation is opened by the thumb of the operator, and in its open state releases the entire lumen of the clamped tube section. For example, the element builds up a tension like a bow in its closed state, which relaxes through releasing of a latch 25a and leads to a rapid opening of the closure 25. Again, a transparent element 23 can adjoin to the handpiece. The portion of the tube, which is installed in the lower end of the bag, comprises two or several lateral openings 26 of large lumen, so that the bag content is received in a most efficient way from the bag and a potential shift of a single terminal lumen of the connector is avoided. The tube portion 9 extends in its open form into the bag and comprises neither a one-way function nor a stool separation function.

Preferably, the balloon as well as the shaft tube of the head unit are made of an elastically deforming material with a preferentially low volume extensibility. For the balloon, especially thin-walled preformed balloon foils of polyurethane (PUR) are preferred, which provide the required combination of a geometrical stability during load and a low membrane-type wall thickness. An elastic expansion of the balloon envelope is not required and in the context of the invention conceptually rather undesirable. The balloon body is preferably filled with air, whereby it adopts in situ a slackly incompletely filled state, which ensures that the filled body in the rectum will, after a phase of adaption, attain a filling pressure, which in a good approximation corresponds to the respective intra-rectal pressure, and therefore allows a nearly pressure-neutral placement, which is comfortable for the patient. The balloon body is preferably formed as a dumbbell, whereby the middle tapered section of the balloon is placed in the anal channel. The balloon body is preferably extruded from a pre-extruded tube material, and in a subsequent step of blow molding shaped to the balloon. In a respective manner, the shaft element supporting the balloon body can be shaped from a pre-extruded foil tube to the required dimensions. Especially, the blow molding enables the shaping of a wavy, corrugated profile.

For both components, PUR types of hardnesses Shore 80A to 95A and 55D to 60D are deployed particularly advantageously, for example the type Pellethane 2363 of the company Lubrizol.

Furthermore, the invention describes a method for the washing of liquid substances or of substances solved in a liquid into the colon of a patient, starting with the insertion of the patient's sided head unit 2 of the device into the anus, whereby the segment 3b, 3c, which is tapered in its diameter, is placed in the region of the sphincter. Then, the balloon body 3 is filled with an amount of air, which is approximately 10 to 20% smaller than the balloon body 3 in a freely unfolded, entirely shaped state of the balloon component. The balloon filled in this manner and clinging slackly to the rectum and anus absorbs the respective force in the rectum and uses it synchronously for the sealing in the anal channel, whereby the trans-anal segment of the balloon envelope follows the respective opening and closing state of the anus. The shaft element 4 supporting the balloon comprises the ability of a radial and axial, elastic folding and straightening. Then, the patient's sided portion of the device is closed by a closing function 19. Subsequently, the connecting of the lavage-type bag for the preparatory cleaning or lavage of the colon takes place. The bag comprises a throttling function as well as a stool separating function. Before the connecting, the lavage bag is closed by the closing function 19 and subsequently is filled up with the lavage fluid. After the opening of the closures on both sides, a lavage-type large fluid volume is instillated into the colon of the patient through a cycling procedure comprising a respective cyclic raising of the bag above and lowering it below the patient's level, which volume entirely comprises 1000 to 1200 mL of fluid, so that it reaches the transversal and potentially even the upper portion of the colon. Therefor, at least 1000 mL of fluid are displaced from the lavage bag into the colon in less than 30 seconds, preferably in less than 15 seconds. After repeating the cycle of inlet and outlet several times, the lavage bag is placed upside down and used as a collecting bag, which, during extended periods of time up to several hours, receives the parts of stool mobilized and drained belatedly after the lavage, without the fear of a perforating injury of the intestines through the head portion remaining in the rectum during the subsequent drainage. After the collection of the mobilized intestinal contents, the lavage bag is disconnected from the head unit, which remains inside the patient's rectum, and is disposed of. The lavage-type cleaning of the colon can be repeated several times, whereby the lavage bag is exchanged each time or is replaced by a fresh bag with fresh fluid. Thereby, the patient's sided part of the device remains inside the patient.

After completion of the preparative lavage of the colon, the bag for the lavage-type instillation of a therapeutical substance or of a transplant is prepared. It is terminally closed by means of the optional closing function 19, then it is filled with the preparation and finally connected to the head portion of the device, which is inside the patient. Through the repetitive lavage-type introduction of the substance from the bag into the colon, analogously to the lavage, again the upper colon parts can be reached. The required flow rates are in the range of 1000 MI in 30 to 15 seconds. In difference to the lavage bag, the bag used for the introduction of the substance or of the transplant comprises a fixed or variably adjustable throttling function, but no stool separating function. After a completed repetitive cycle of inflow and outflow of the substance to be introduced, the preparation can remain inside the patient for a duration several hours, variably adjustable by the applicant, without any leakage of the preparation out from the anus. Thereby, the patient can adopt a comfortable, semisitting or sitting posture. For the final outflow of the preparation from the colon, the bag is lowered below the level of the patient and rests there until the substance is completely secreted.

The invention claimed is:

1. Method for flushing of liquid substances or of substances dissolved in a liquid or of a stool transplant suspended in a liquid into the colon of a patient, comprising the following steps:
    a) introducing a patient-sided head part (2) of a device into the anus, so that a segment (3b, 3c) of a balloon body with tapered diameter is placed in the area of the sphincter so as to be disposed in a trans-anal position;
    b) filling the balloon body (3) for the purpose of trans-anal sealing and fixation of the device with an air volume, in which the air volume is approximately 10 to 20% lower than the volume of the balloon body in a freely unfolded, entirely shaped state;
    c) connecting a lavage bag for a preparatory cleaning or lavage of the colon to the patient-sided head part (2);
    d) raising the lavage bag above the level of the patient's anus, with opened closure on a patient side of the lavage bag, so as to introduce a large liquid volume with a flush into the colon of the patient;
    e) turning the lavage bag upside down and lowering the lavage bag below the level of the patient's anus, and then using the lavage bag as a collection bag;
    f) connecting a bag for lavage introduction of a therapeutic substance or of a transplant to the patient-sided head part (2);
    g) raising the bag for the lavage introduction of a therapeutic substance or of the transplant above the level of the patient's anus, with opened closure on a patient side of the bag for introducing the volume of the therapeutic substance or of the transplant as a flush into the colon of the patient.

2. Method according to claim 1, characterized in that, before or during one of steps a) to c), the patient-sided head part (2) is closed or is being closed by a closing functional element (19).

3. Method according to claim 1, characterized in that, during one of steps d) or e), the lavage bag is raised above the level of the patient's anus and is subsequently lowered below the level of the patient's anus in an alternating or cyclic mode.

4. Method according to claim 3, characterized by multiple repetitions of raising the lavage bag above the level of the patient's anus and subsequently lowering the lavage bag below the level of the patient's anus, and further wherein the lavage bag is exchanged and replaced by a fresh lavage bag containing fresh liquid, while the patient-sided head part (2) remains inside the patient.

5. Method according to claim 1, characterized in that, after step e), the lavage bag is separated from the patient-sided head part (2), which patient-sided head part remains in the patient's anus, and the lavage bag separated from the patient-sided head part is disposed of.

6. Method according to claim 1, characterized in that, before step f), the bag for the lavage introduction of the therapeutic substance or of the transplant is closed or is going to be closed by a closing functional element (19).

7. Method according to claim 6, characterized in that, before step f), the bag for the lavage introduction of the therapeutic substance or of the transplant is filled in its closed state with the therapeutic substance or with the transplant.

8. Method according to claim 1, characterized in that the lavage bag is provided with an inflow throttling function and with a separation function, which prevents stool already disposed in the lavage bag from flowing into the colon of the patient.

9. Method according to claim 1, characterized in that the lavage bag is provided with a closing functional element (19) which is closed before filling the lavage bag with the large liquid volume and is opened only after connection to the patient-sided head part (2).

10. Method according to claim 1, characterized in that the lavage bag or the bag for the lavage introduction of the therapeutic substance or of the transplant is used, having a filling volume of 1000 to 2000 mL in total, so that the large liquid volume reaches the transversal portion of the colon and eventually also the ascending portion of the colon, whereby at least 1000 mL flow to the colon of the patient in less than 30 seconds.

11. Method according to claim 1, characterized by a repetitive lavage introduction of the therapeutic substance or of the transplant from the bag for the lavage introduction of the therapeutic substance or of the transplant into the colon of the patient.

12. Method according to claim 11, characterized in that, after a completed repetitive cycle of inflow and outflow of the therapeutic substance or the transplant, the therapeutic substance or the transplant remains inside the patient for several hours, variably definable by the user, without a leakage of the therapeutic substance or of the transplant out of the anus of the patient.

13. Method according to claim 1, characterized in that flow values are in a range of 1000 mL in 15 to 10 seconds.

14. Method according to claim 1, characterized in that the bag used for the lavage introduction of the therapeutic substance or of the transplant is provided with a fixed or adjustable throttle function, but is not provided with a stool separating function.

15. Method according to claim 1, characterized in that, for a subsequent draining of the therapeutic substance or of the transplant out of the colon, the lavage bag is lowered to the level below the patient's anus and maintained at the level below the patient's anus until the therapeutic substance or the transplant has completely drained out of the colon of the patient.

* * * * *